US011607116B2

(12) United States Patent
Tsai et al.

(10) Patent No.: US 11,607,116 B2
(45) Date of Patent: Mar. 21, 2023

(54) ENDOSCOPIC DEVICE HAVING A ROTATIONAL OPTICAL ELEMENT

(71) Applicant: Broad Perspect Biomedical Technology Co., Ltd., New Taipei (TW)

(72) Inventors: Tsang-Chou Tsai, New Taipei (TW); John Huang, New Taipei (TW)

(73) Assignee: BROAD PERSPECT BIOMEDICAL TECHNOLOGY CO., LTD., New Taipei (TW)

(*) Notice: Subject to any disclaimer, the term of this patent is extended or adjusted under 35 U.S.C. 154(b) by 287 days.

(21) Appl. No.: 17/029,059

(22) Filed: Sep. 23, 2020

(65) Prior Publication Data
US 2022/0087516 A1    Mar. 24, 2022

(51) Int. Cl.
*A61B 1/00*    (2006.01)
(52) U.S. Cl.
CPC ...... *A61B 1/00174* (2013.01); *A61B 1/00006* (2013.01); *A61B 1/0016* (2013.01); *A61B 1/00096* (2013.01)
(58) Field of Classification Search
CPC ............ A61B 1/00174; A61B 1/00006; A61B 1/00096; A61B 1/0016; A61B 1/00148; A61B 1/00149; A61B 1/00154; A61B 1/00183; B25J 7/00; A63H 1/06
See application file for complete search history.

(56) References Cited

U.S. PATENT DOCUMENTS

| 5,904,690 A | * | 5/1999 | Middleman | A61B 17/29 606/113 |
| 2001/0052930 A1 | * | 12/2001 | Adair | H04N 7/142 348/E3.019 |
| 2002/0148349 A1 | * | 10/2002 | Kendall | F15B 15/224 92/28 |
| 2020/0146539 A1 | * | 5/2020 | Hirono | A61B 1/00183 |
| 2022/0160458 A1 | * | 5/2022 | Tadano | A61B 34/37 |

FOREIGN PATENT DOCUMENTS

JP    2004181257    *    7/2004    ............ A61B 19/02

* cited by examiner

*Primary Examiner* — Timothy J Neal
*Assistant Examiner* — James Edward Boice
(74) *Attorney, Agent, or Firm* — Leong C. Lei (57) ABSTRACT

The endoscopic device includes a main member having a front slot and a shaft member having a spiral strip selectively running through the slot. The spiral strip is connected to a rotational element whose front end is provided with an optical element. A camera support element is extended from the main member and a camera element is supported by the camera support element. By running the spiral strip through the slot to turn the rotational element and the optical element, a viewing direction of the camera element is altered by the optical element.

4 Claims, 11 Drawing Sheets

ENDOSCOPIC DEVICE HAVING A ROTATIONAL OPTICAL ELEMENT

BACKGROUND OF THE INVENTION

(a) Technical Field of the Invention

The present invention is generally related to endoscopy, and more particular to an endoscopic device.

(b) Description of the Prior Art

Minimally invasive surgery in an increasingly popular medical procedure. It involves surgical techniques that reduce the size of incisions and, as such, the associated pain, risk of infection, and healing time.

Endoscopes are commonly used in minimally invasive surgery. An endoscope is usually small and complex and it is therefore costlier and more difficult to operate.

SUMMARY OF THE INVENTION

A major feature of the present invention is to turn a shaft member by running a spiral strip through a slot so as to turn an optical element and, therefore, change a view direction of a camera element.

The endoscopic device includes a main member having a front slot and a shaft member having a spiral strip selectively running through the slot. The spiral strip is connected to a rotational element whose front end is provided with an optical element. A camera support element is extended from the main member and a camera element is supported by the camera support element.

By running the spiral strip through the slot to turn the rotational element and the optical element, a viewing direction of the camera element is altered by the optical element.

Therefore, with the sole control to the spiral strip of the shaft member, the viewing direction of the camera element may be altered conveniently. This mechanism has a simple structure and, therefore, a reduced manufacturing cost.

The present invention, as such, may obviate the complex structure problem of conventional endoscopic devices for minimally invasive surgery.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
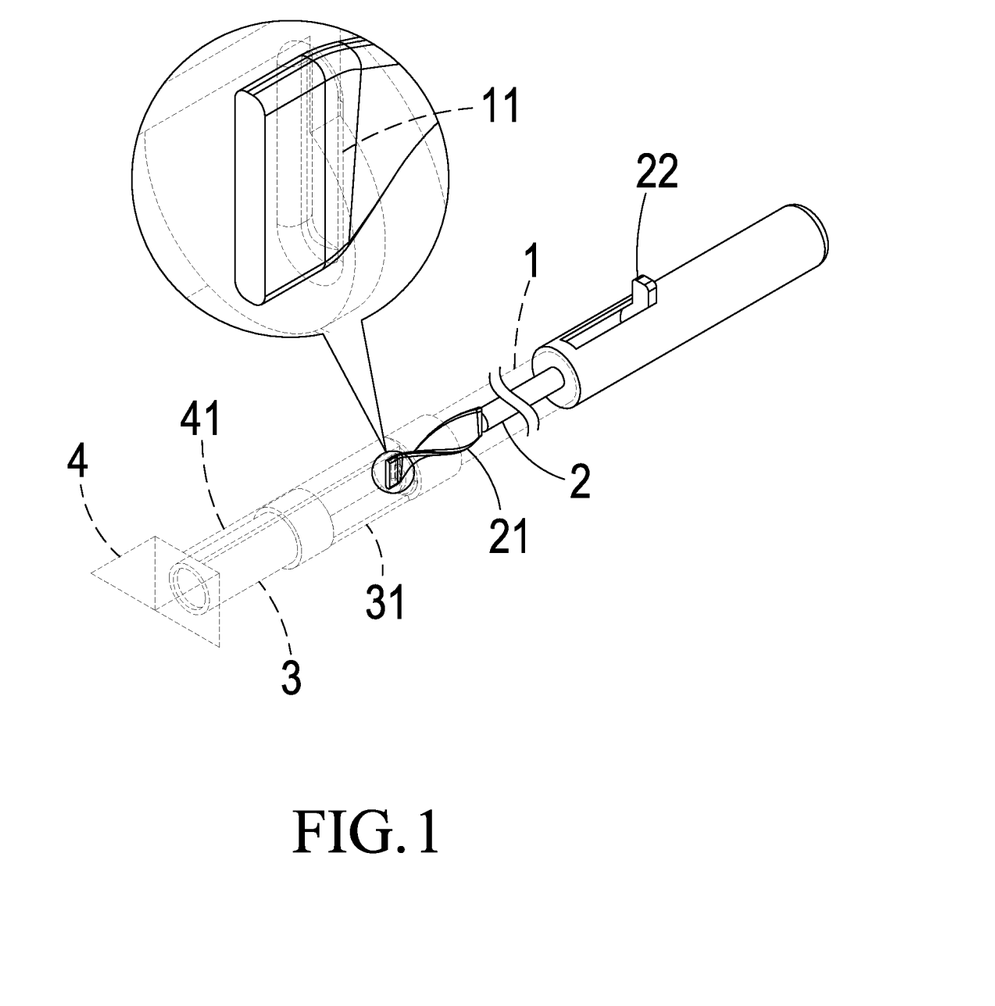
FIG. 1 is a perspective schematic diagram showing an endoscopic device according to a first embodiment of the present invention.
Figure 2:
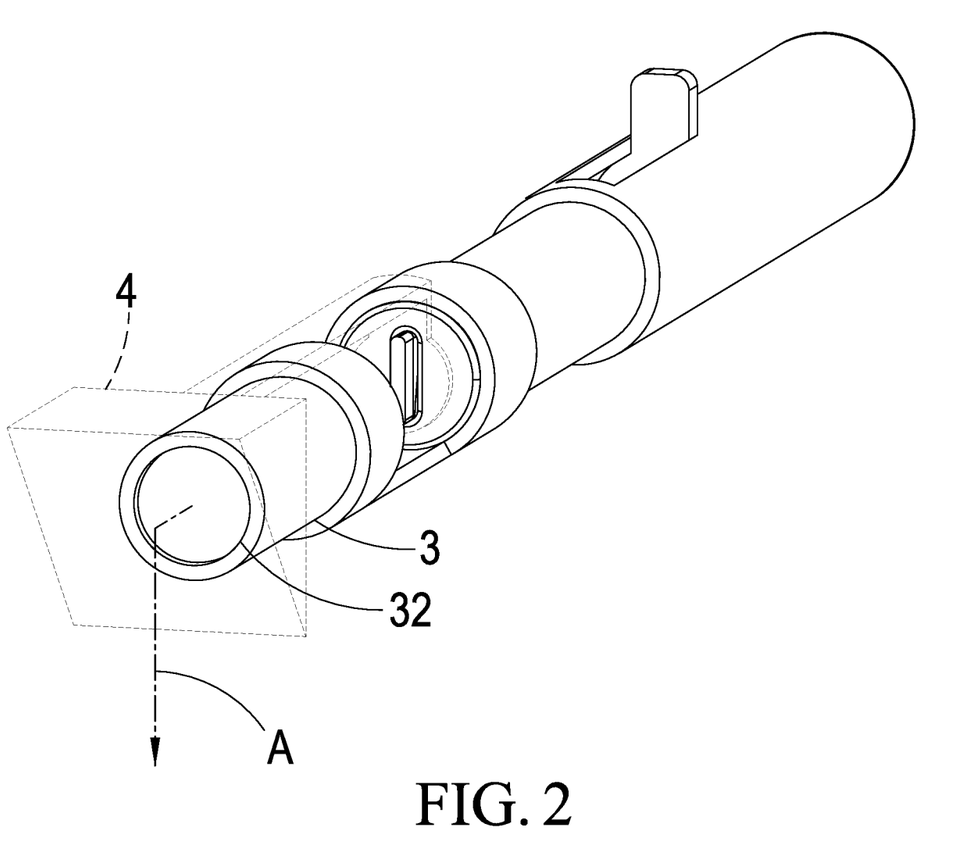
FIG. 2 is a perspective schematic diagram showing an optical element positioned in front of a camera element of the endoscopic device of FIG. 1.

As shown in FIGS. 1 and 2, an endoscopic device according to a first embodiment of the present invention includes:

a main member 1 that, in the present embodiment, has a tubular shape and a through slot 11 on a front side;

a shaft member 2 housed in the main member 1 including at least a spiral strip 21 extended axially inside the main member 1 and selectively through the slot 11 where, in the present embodiment, the slot 11 has an elongated shape and the spiral strip 21 is a twisted strip having a cross-section compatible with that of the slot 11;

a U-shaped camera support element 31 whose back section is sleeved over a front section of the main member 1;

a camera element 3 joined to a front end of the camera support element 31;

a L-shaped rotational element 41 whose back end is joined to a front end of the spiral strip 21;

an optical element 4 on a front end of the rotational element 41 where the rotational element 41 has an appropriate length so that the optical element 4 is positioned in front of a lens 32 of the camera element 3 and, in the present embodiment, the optical element 4 is a prism so that the camera element 3 may capture images along a direction A; and a lever 22 extended from the shaft member 2, where in the present embodiment, the lever 22 is a radial protrusion from the shaft member 2 out of the main member 1.

The operation of the endoscopic device is described as follows.

As shown in FIGS. 1 to 5, the endoscopic device intrudes into a human body and then the camera element 3 of the endoscopic device is used to observe or capture images of the inside of the human body to facilitate surgery or examination.

Figure 3:
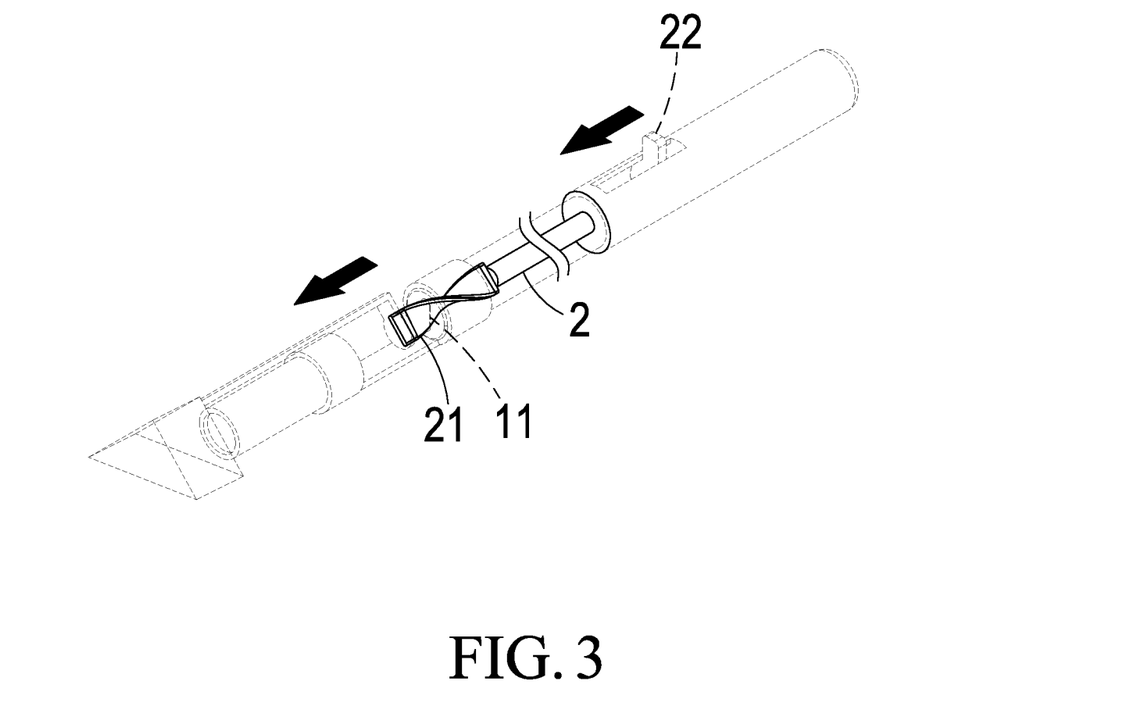
FIG. 3 is a perspective schematic diagram showing a lever is engaged to move a spiral strip through a slot of the endoscopic device of FIG. 1.
Figure 4:
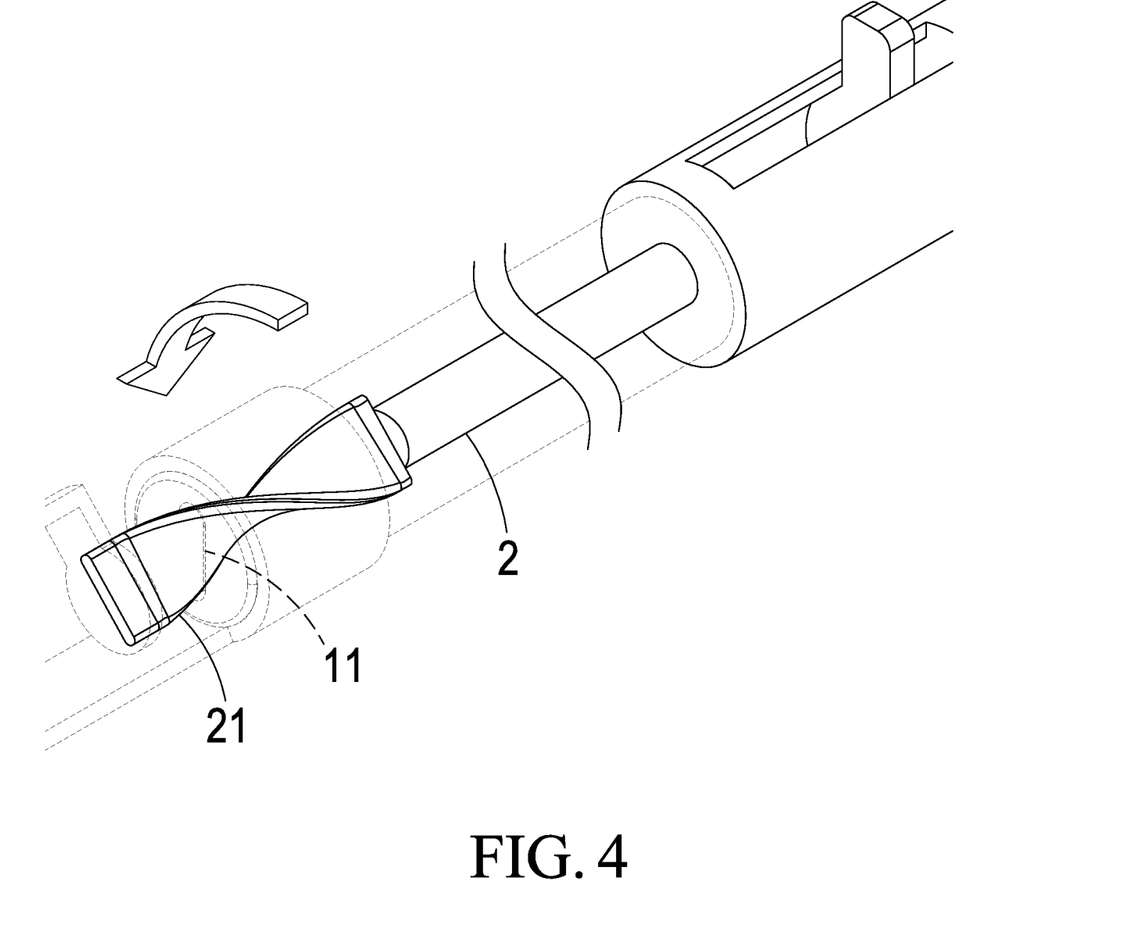
FIG. 4 is a perspective schematic diagram showing the spiral strip is run through the slot of FIG. 3.
Figure 5:
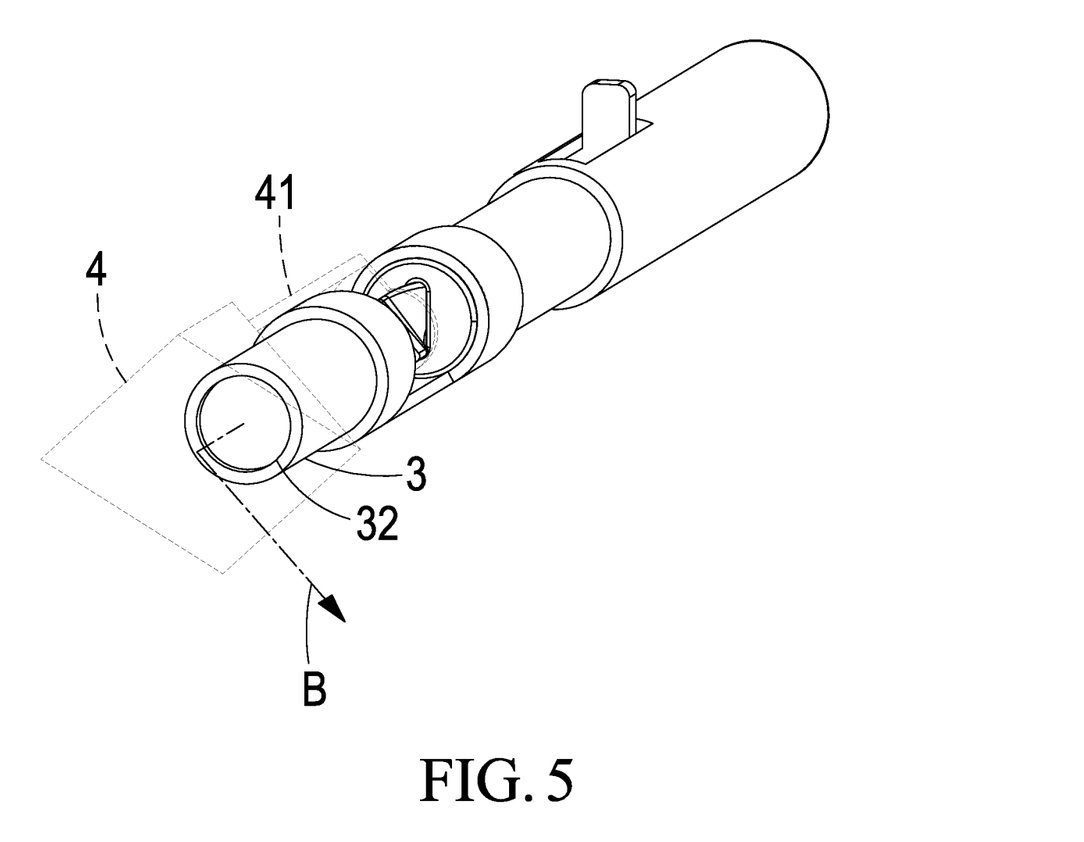
FIG. 5 is a perspective schematic diagram showing an optical element has a view direction altered as the spiral strip is run through the slot of FIG. 4.

To change a viewing direction of the camera element 3, the lever 22 is pushed forward to move the shaft member 2 toward a front direction. In the meantime, the spiral strip 21 is extended out of the slot 11. As shown in FIGS. 3 and 4, as the spiral strip 21 passes through the slot 11, the rotational element 41 is rotated as well. Therefore, the optical element 4 is also turned in front of the lens 32 of the camera element 3. As such, the viewing direction of the camera element 3 is varied as the optical element 4 spins. For example, the viewing direction of the camera element 3 may vary from the direction A shown in FIG. 2 to another direction B shown in FIG. 5. Through the simple and cost-effective structure taught by the present invention, a user of the endoscopic device may easily and conveniently alter the viewing direction of the camera element 3.

Figure 6:
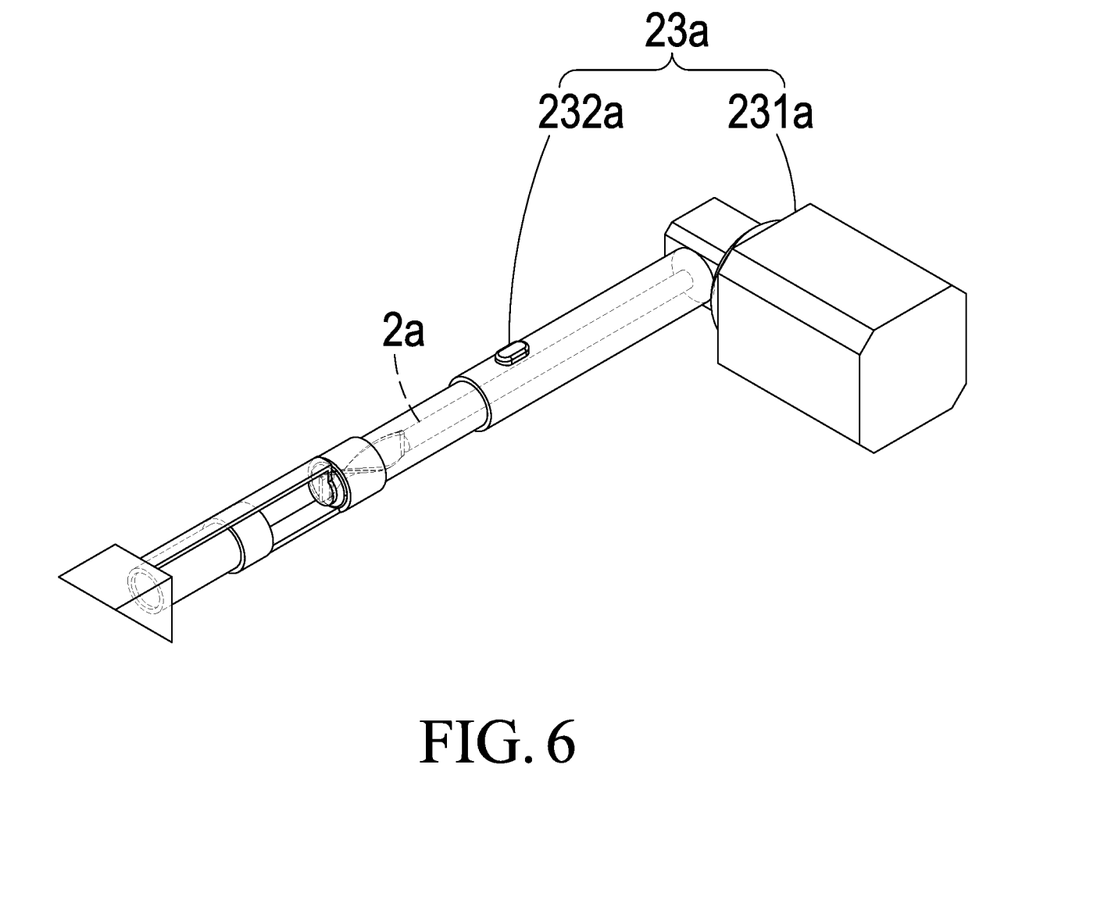
FIG. 6 is a perspective schematic diagram showing an endoscopic device according to a second embodiment of the present invention.

As shown in FIG. 6, a second embodiment of the present invention is similar to the previous embodiment except that the shaft member 2a is operated by a driving member 23a which, in the present embodiment, includes a servo motor 231a engaging the shaft member 2a and a control button 232a controlling the servo motor 231a. By operating the control button 232a, the servo motor 231a is controlled to drive shaft member 2a to move. This demonstrates that the shaft member 2a may be driven in various manners.

As shown in FIGS. 7 to 11, a third embodiment of the present invention is similar to the previous embodiments. In the present embodiment, the main member 1b's back end is joined to a front end of a first extension member 5b. A back end of the first extension member 5b that is away from the main member 1b is pin-joined to a front end of a first connection member 61b. A back end of the first connection member 61b that is away from the first extension member 5b is pin-joined to a back end of a second extension member 7b. A front end of the second extension member 7b is pin-joined to a middle section of the first extension member 5b. The back end of the first connection member 61b is also pin joined to front ends of a second connection member 62b and a third connection member 63b. A back end of the second connection member 62b is pin-joined to a front end of a first control member 81b by a second pivot 621b. A second control member 82b is slidably mounted on the first control member 81b. A back end of the third connection member 63b is pin-joined to a front end of the second control member 82b and a middle section of the third connection member 63b is also pin-joined to first control member 81b by a third pivot 631b.

Figure 7:
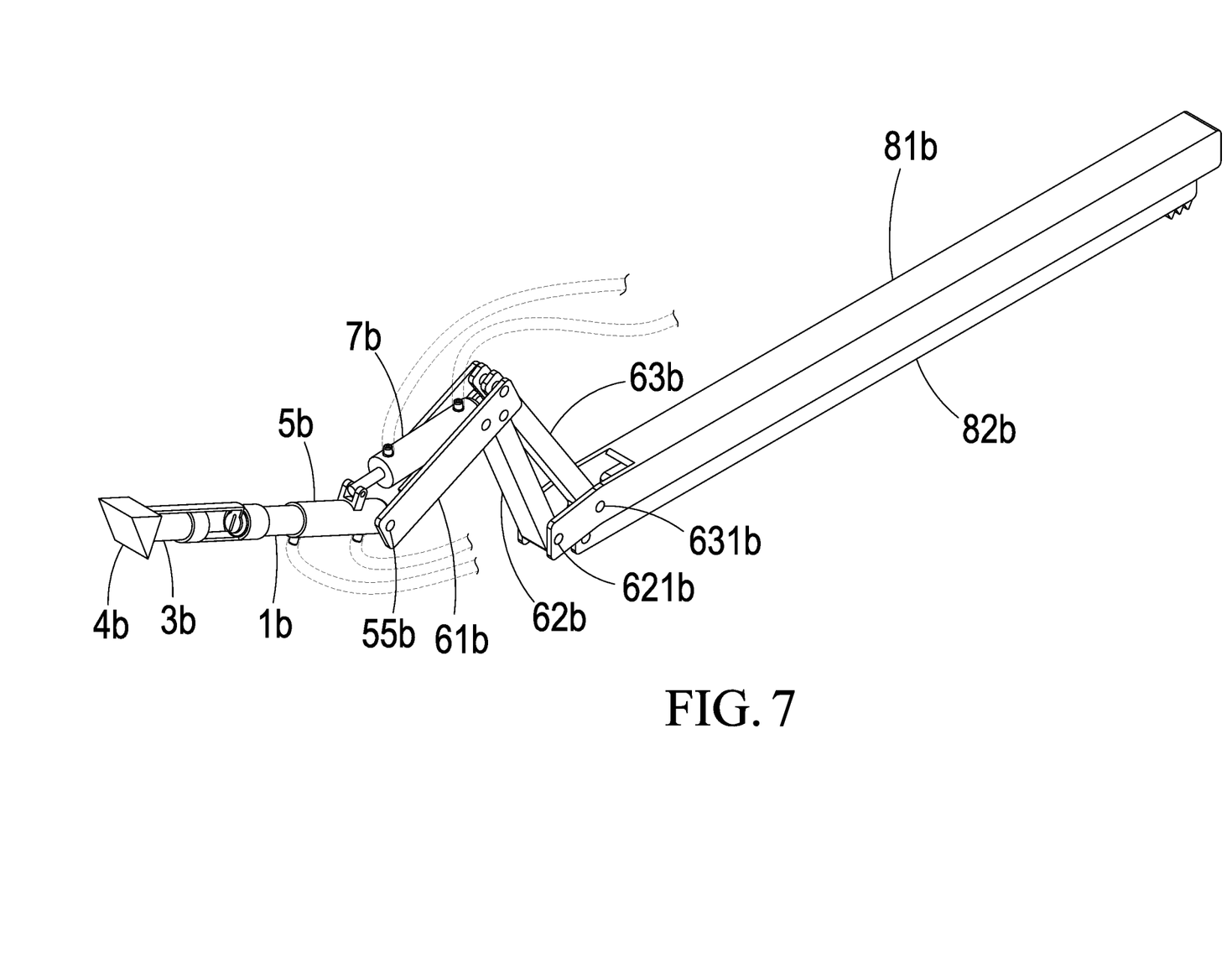
FIG. 7 is a perspective schematic diagram showing an endoscopic device according to a third embodiment of the present invention.
Figure 8:
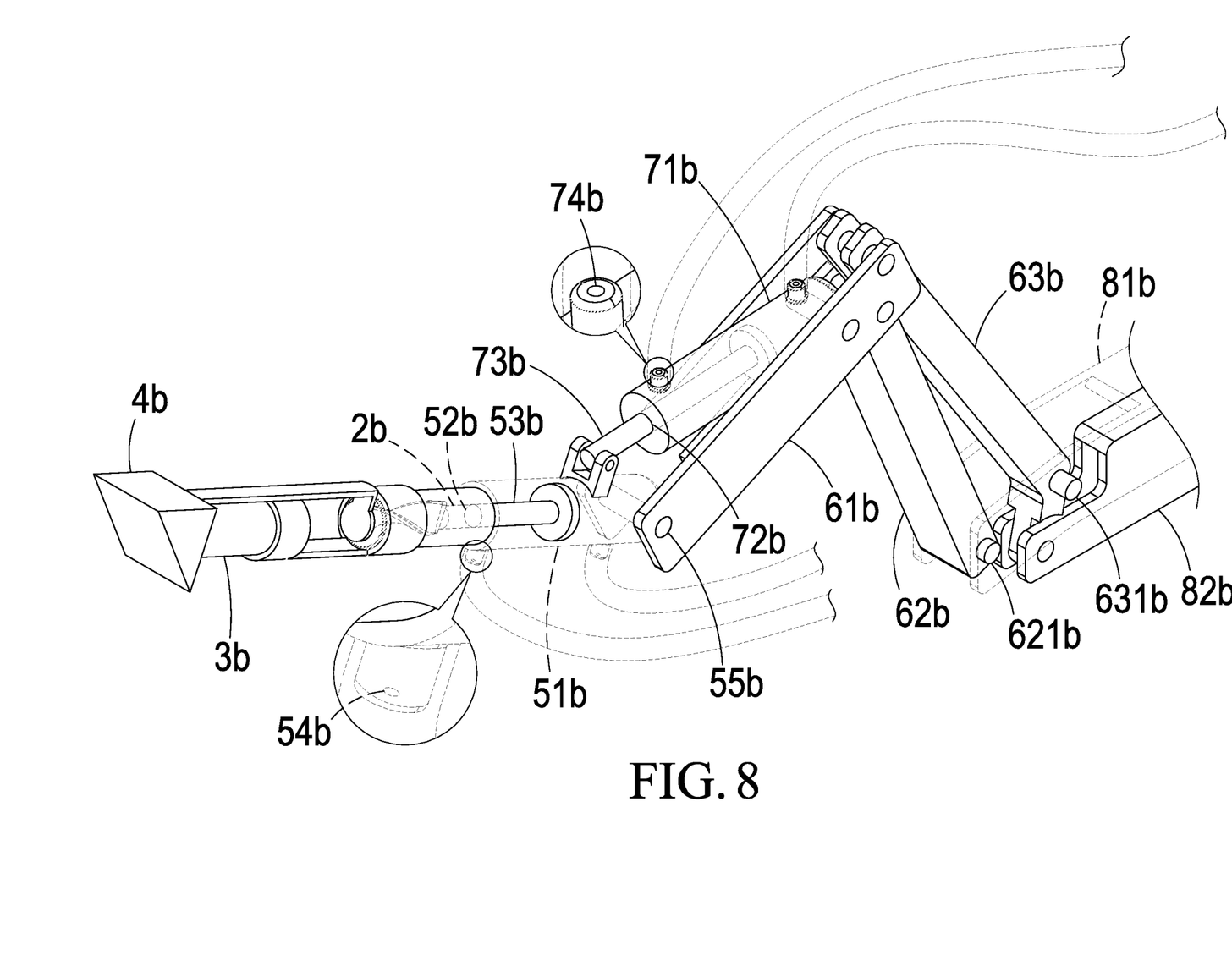
FIG. 8 is a perspective schematic diagram that partially enlarges the endoscopic device of FIG. 7.

Both first extension member 5b and second extension member 7b are pressure-based devices. The first extension member 5b includes a first cylinder 51b, a first opening 52b, a first shaft 53b, and a number of first through holes 54b. The first opening 52b is provided at a front end of the first cylinder 51ba. A back end of the first cylinder 51b is pin joined to the front end of the first connection member 61b by a first pivot 55b. The first shaft 53b is slidably housed in the first cylinder 51b and a front end of the first shaft 53b may selectively run through the first opening 52b. The front end of the first shaft 53b is joined to a back end of shaft member 2b. The first through holes 54b are formed on the first cylinder 51b through which liquid or air is introduced into or drawn from the first cylinder 51b to extend or retract the first shaft 53b inside the first cylinder 51b.

The second extension member 7b includes a second cylinder 71b, a second opening 72b, a second shaft 73b, and a number of second through holes 74b. The second extension member 7b is structured and operated similarly to those of the first extension member 5b. The difference lies in that the second shaft 73b is pin-joined to the first extension member 5b, and the second cylinder 71b is pin-joined to the first connection member 61b. The second extension member 7b, therefore, may drive the first extension member 5b to turn.

Figure 9:
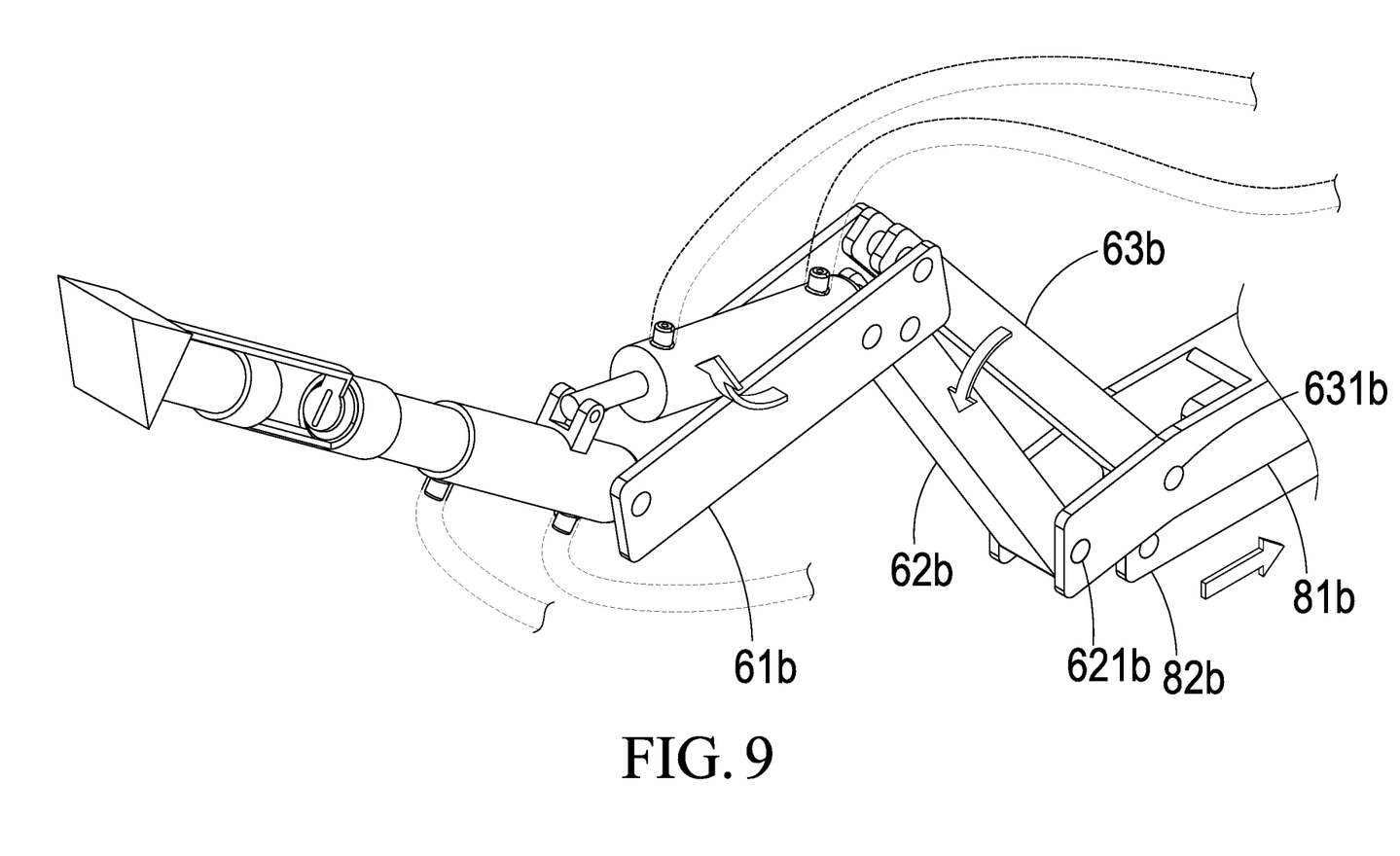
FIG. 9 is a perspective schematic diagram showing a scenario of the endoscopic device of FIG. 7.
Figure 10:
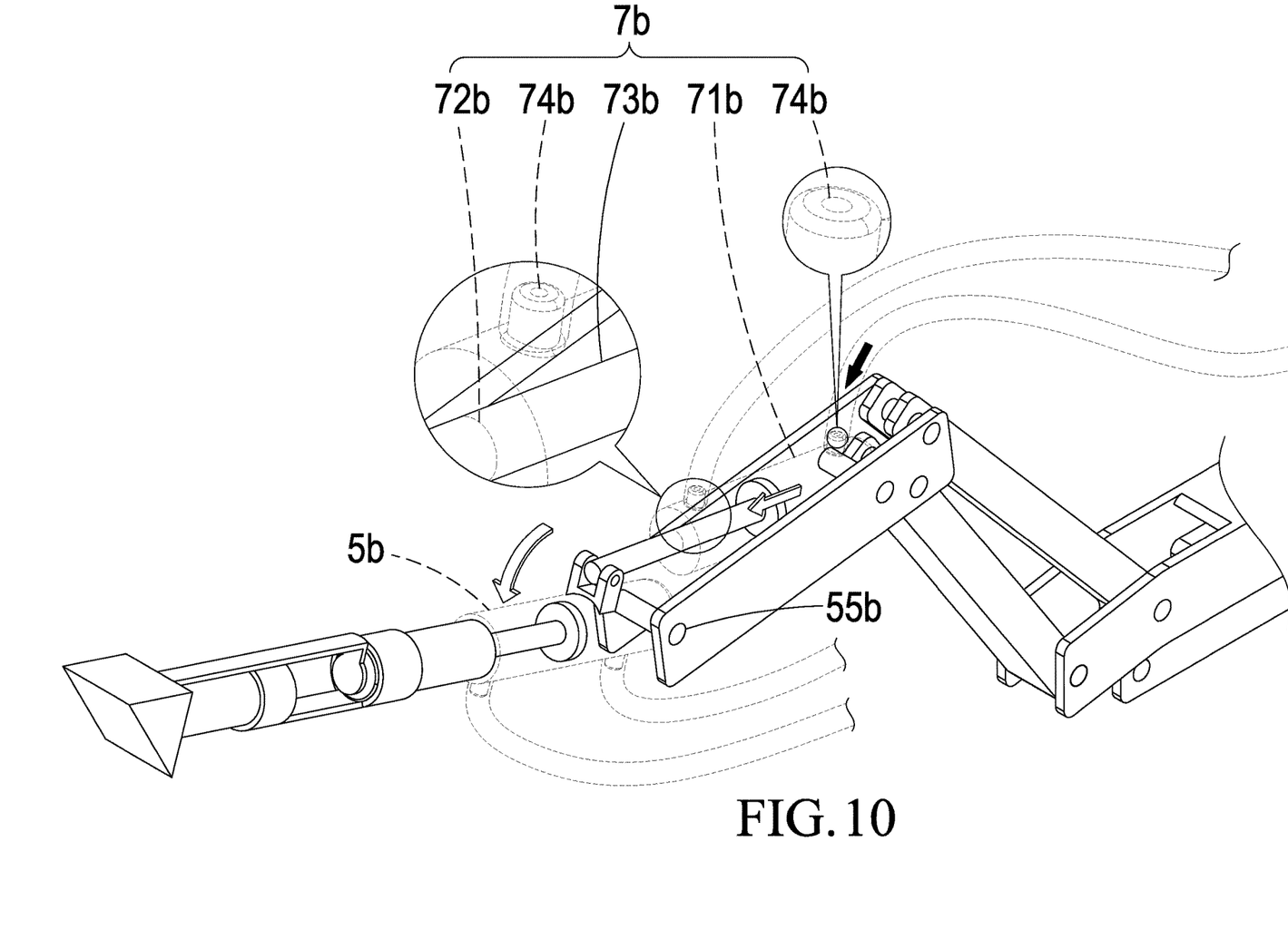
FIG. 10 is a perspective schematic diagram showing another scenario of the endoscopic device of FIG. 7.
Figure 11:
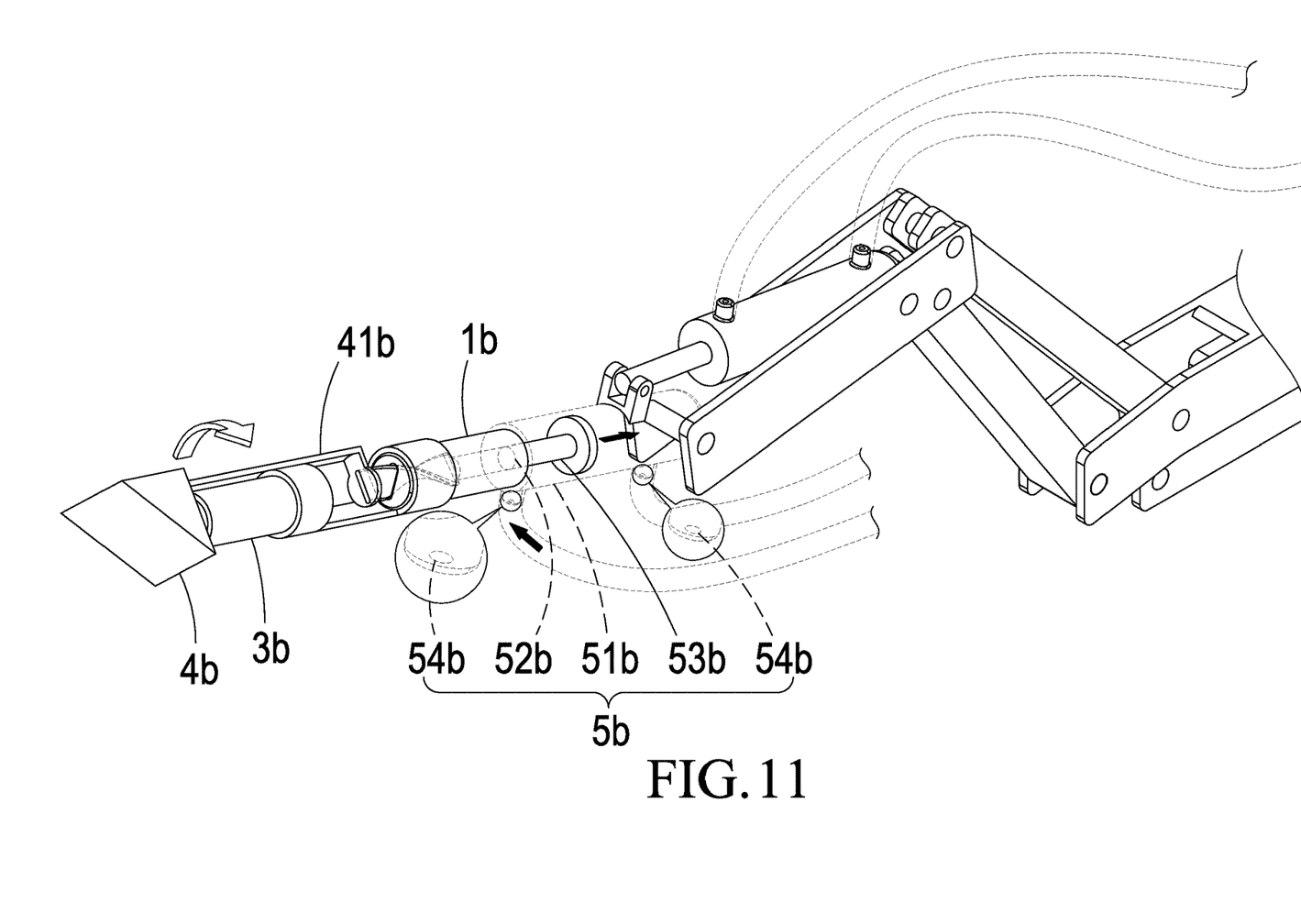
FIG. 11 is a perspective schematic diagram showing another scenario of the endoscopic device of FIG. 7.

As shown in FIG. 9, when the second control member 82b moves backward relative to the first control member 81b, the second connection member 62b turns counterclockwise around the second pivot 621b, and the third connection member 63b turns counterclockwise around the third pivot 631b. As the second connection member 62b and third connection member 63b spin counterclockwise, the first connection member 61b turns clockwise. However, when the second control member 82b moves forward relative to the first control member 81b, the first connection member 61b, second connection member 62b, and third connection member 63b would turn the opposite way. As shown in FIG. 10, liquid or air may be injected into or drawn out of the second cylinder 71b through the second through holes 74b to extend or retract the second shaft 73b through the second opening 72b. When the second extension member 7b is extended, the first extension member 5b is turned counterclockwise around the first pivot 55b. When it is retracted, the first extension member 5b is turned clockwise. As shown in FIG. 11, liquid or air may be injected into or drawn out of the first cylinder 51b through the first through holes 54b to extend or retract the first shaft 53b through the first opening 52b. When first extension member 5b is extended or retracted, the shaft member 2b is moved forward or backward, thereby turning the rotational element 41b as well as the optical element 4b.

As described above, the camera element 3b of the endoscopic device maybe quickly adjusted to achieve enhanced operation convenience and efficiency.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the claims of the present invention.

We claim:

1. An endoscopic device, comprising:
   a main member having a through slot on a front side;
   a shaft member housed in the main member comprising a spiral strip extended axially inside the main member and selectively moved through the slot;
   a camera support element whose back section is sleeved over a front section of the main member;
   a camera element joined to a front end of the camera support element;
   a rotational element whose back end is joined to a front end of the spiral strip, where, when the spiral strip is extended through the slot, the rotation element is turned by the spiral strip; and
   an optical element on a front end of the rotational element, where the optical element is positioned in front of a lens of the camera element, and, when the optical element is turned along with the rotational element, a viewing direction of the camera element is changed by the optical element;
   wherein the main member is joined to a first extension member;

wherein a back end of the first extension member that is away from the main member is pin-joined to a front end of a first connection member;

wherein a back end of the first connection member that is away from the first extension member is pin-joined to a back end of a second extension member; and a front end of the second extension member is pin-joined to a middle section of the first extension member;

wherein a back end of the first connection member is pin-joined to front ends of a second connection member and a third connection member;

wherein a back end of the second connection member is pin-joined to a front end of a first control member; and a middle section of the third connection member is pin-joined to a middle section of the first control member; and wherein a second control member is slidably mounted on the first control member; and a back end of the third connection member is pin-joined to a front end of the second control member.

2. The endoscopic device according to claim 1, wherein the shaft member is driven by a driving member.

3. The endoscopic device according to claim 1, wherein the first extension member comprises a first cylinder, a first opening, a first shaft, and a plurality of first through holes; a front end of the first extension member is joined to a back end of the main member; the first opening is provided at a front end of the first cylinder; the first shaft is slidably housed in the first cylinder; a front end of the first shaft selectively runs through the first opening; the front end of the first shaft is joined to a back end of the shaft member; and the first through holes are formed on the first cylinder.

4. The endoscopic device according to claim 1, wherein the second extension member comprises a second cylinder, a second opening, a second shaft, and a plurality of second through holes; the second opening is provided at a front end of the second cylinder; the second shaft is slidably housed in the second cylinder; a front end of the second shaft selectively runs through the second opening; the front end of the second shaft is pin-joined to the middle section of the first extension member; and the second through holes are formed on the second cylinder.

* * * * *